United States Patent [19]

Orlando et al.

[11] Patent Number: 5,262,180
[45] Date of Patent: Nov. 16, 1993

[54] METHOD FOR TREATING ACUTE ALKALI EXPOSURE WITH CARBON DIOXIDE

[75] Inventors: Roy C. Orlando; R. Lee Meyers, both of Chapel Hill, N.C.

[73] Assignee: University of North Carolina at Chapel Hill, Chapel Hill, N.C.

[21] Appl. No.: 797,781

[22] Filed: Nov. 25, 1991

Related U.S. Application Data

[63] Continuation-in-part of Ser. No. 685,413, Apr. 15, 1991, abandoned.

[51] Int. Cl.$^5$ .............................................. A61K 33/00
[52] U.S. Cl. ................................ 424/700; 424/DIG. 13
[58] Field of Search ....................... 424/DIG. 13, 700

[56] References Cited

U.S. PATENT DOCUMENTS

| | | | |
|---|---|---|---|
| 1,599,883 | 9/1926 | Gilchrist | 604/23 |
| 3,121,663 | 2/1964 | Parker | 167/64 |
| 3,876,773 | 4/1975 | Bracken | 424/161 |
| 4,608,257 | 8/1986 | Teeter | 424/166 |
| 4,676,774 | 6/1987 | Semm et al. | 604/26 |
| 4,678,661 | 7/1987 | Gergely et al. | 424/44 |
| 4,735,603 | 4/1988 | Goodson et al. | 604/21 |

FOREIGN PATENT DOCUMENTS

| | | |
|---|---|---|
| 1964350 | 7/1971 | Fed. Rep. of Germany . |
| 59-141512 | 8/1984 | Japan . |
| 61-53215 | 3/1986 | Japan . |
| 1017335 | 5/1983 | U.S.S.R. . |
| 1396772 | 6/1975 | United Kingdom . |

OTHER PUBLICATIONS

Cotzhauzen "Gleanings from the German Journals" Am J. Pharm, pp. 318, and 319 Jun. 1880.
Merck Manual "Respiratory Alkalosis", pp. 951–952, 1982.
The Merck Manual, 14th Ed., pp. 1877–1879 (1982).

Primary Examiner—Frederick E. Waddell
Assistant Examiner—Gregory Hook
Attorney, Agent, or Firm—Bell, Seltzer, Park & Gibson

[57] ABSTRACT

The present invention provides a method for combatting damage to a body tissue contacted to an alkali. The method comprising administering $CO_2$ to the subject in an amount sufficient to produce an acidotic state in the tissue, the acidotic state serving to prevent alkali damage to the tissue. In a preferred embodiment of the invention, a subject is caused to inhale a mixture of 95%$O_2$ and 5%$CO_2$ for brief periods of time, followed by periods of breathing room air. The invention is particularly useful for treating alkaline injury of the esophagus caused by ingestion of alkaline material.

17 Claims, 3 Drawing Sheets

METHOD FOR TREATING ACUTE ALKALI EXPOSURE WITH CARBON DIOXIDE

This invention was made with government support under Grant No. 5-R01-DK35013 from the National Institute of Health. The government may have certain rights to the invention.

RELATED APPLICATIONS

This application is a continuation-in-part of copending U.S. patent application Ser. No. 7/685,413, filed Apr. 15, 1991, now abandoned.

FIELD OF THE INVENTION

This invention, in general, relates to a method for the treatment of acute alkali exposure in subjects in need of such treatment by the administration of carbon dioxide ($CO_2$) -rich gas mixtures.

BACKGROUND OF THE INVENTION

Caustic alkaline materials, such as NaOH, KOH and $Na_2CO_3$ and the like, are often used as reagents in medical test kits, research laboratories and industrial processes and as cleaning agents (e.g. drain cleaners, washing powders, soaps). Because of the wide usage and availability of such materials, toxic exposures occur with reasonable frequency. Accidental exposure from the ingestion of caustic alkali is a particularly serious problem among children. In the United States at least 5000 serious ingestions of caustic alkali occur each year among children. The consequences from ingestion may occur acutely with esophageal wall necrosis leading to esophageal perforation and death; subacutely to esophageal obstruction from stricture formation; or chronically to an increased risk of developing esophageal squamous cell carcinoma. See L. Leape et al., *N. Engl. J. Med.* 284, 578–81 (1971); P. Loeb and A. Eisenstein, in: *Gastrointestinal Disease: Pathophysiology, Diagnosis, Management*, 148-155 (M. Sleisenger and J. Fordtran Eds. 1983)(WB Saunders Company, Philadelphia, Pa.). Chemical burns resulting from caustic alkali splashing onto skin and into the eye are also serious problems associated with accidental exposure. The former potentially leads to disfigurement and the latter to blindness from corneal ulceration (Advanced Trauma Life Support Course, American College of Surgeons Committee on Trauma; 1989; page 208).

The damage caused by the exposure of body tissues to caustic alkali is due to the high pH of such substances. Treatments of alkali exposure, therefore, focus on the reduction of pH towards normal (pH 7.4) as quickly as possible. With external surfaces of the body, e.g. skin and eye, washing with water (known as hydrotherapy in the case of corneal burns) is the major method used to reduce tissue pH. In such cases, the water dilutes and removes the alkaline material. There is data, however, indicating that even after a single exposure of alkali to skin, a stratified squamous epithelial-lined organ, the alkalinity of the tissue remains high for many hours (>12 hours). See R. Gruber et al., *Plast. Reconstr. Surg.* 55, 200 (1975). Such prolonged tissue alkalinity is reportedly due to the propensity of alkali to form soluble protein-hydroxyl ion complexes that serve to further permit the penetration of alkali into the underlying tissue. M. Kirsh and F. Ritter, *Ann. Thorac. Surg.* 21, 74–82 (1976). For this reason, continued washing (or hydrotherapy in the case of corneal burns) for many hours has been recommended to reduce the degree of alkaline injury.

For caustic alkali ingestions, the major risk of damage is to the stratified squamous epithelial-linings of the oral cavity and esophagus. The recommended treatment for oral contact of a caustic alkali, for example lye, is washing with water. In contrast, there is no general agreement on the treatment of lye exposure to esophagus. Some suggest the immediate ingestion of weakly acidic substances, e.g. vinegar, to neutralize the alkali. Others suggest this not be done because of the concern that dilution and neutralization of alkali by weak acids may yield enough heat from an exothermic reaction to increase, not decrease, the degree of tissue injury and that in severe burns of the esophageal wall such attempts will cause the patient to gag, wretch, vomit and in so doing aspirate or convert the burned and weakened esophageal wall into a perforation risking death acutely from mediastinitis. P. Loeb and A. Eisenstein AM, supra. B. Rumack and J. Burrington, *Clin. Toxicol.* 11, 27–34 (1977). Therefore, at present the majority view recommends "nothing by mouth" as therapy for lye ingestion.

The majority of serious lye ingestions do not lead to esophageal perforations and death. Thus the most serious concern, and most common complication, is the development of an esophageal stricture. Esophageal stricture results from transepithelial necrosis and healing by scar (fibrosis) formation. For this reason current therapeutic approaches focus less on trying to reduce the degree of acute injury than on trying to prevent stricture formation, even though it is recognized that the major determinant of stricture formation is the depth and extent of the acute injury. To date, however, no agent has proven beneficial. Even the administration of corticosteriods was recently documented to be of no benefit in reducing stricture formation. See K. Anderson et al., *New Engl. J. Med.* 323, 637–640 (1990).

From the foregoing it is evident that a rapid, safe and effective means of reducing tissue alkalinity after exposure of skin, eye, mouth, oral cavity, esophagus, and other tissues, to caustic alkaline substances is sorely needed to reduce the morbidity (and in some cases mortality) from this disorder.

SUMMARY OF THE INVENTION

The present invention provides just such a means of rapidly, safely and effectively reducing tissue alkalinity. The inventors, while carrying out investigations on the mechanisms of alkali injury to the stratified squamous epithelium of rabbit esophagus, have identified a method for combating damage to a body tissue in contact with alkali in a subject in need of such treatment. The present invention is based on the therapeutic use of exogenously administered $CO_2$ through inhalation of gas mixtures rich in $CO_2$ to create a mild blood, tissue and body cavity acidosis to reduce damage done to tissues exposed to caustic alkali.

Accordingly, the present invention provides a method for combating damage to a body tissue contacted to an alkali in a subject, including human subjects, in need of such treatment. The method comprises the administration of $CO_2$ to the subject in an amount effective to produce an acidotic state in the tissue contacted to the alkali. The acidotic state serves to prevent alkali damage to the tissue.

The acidotic state produced according to the invention may be a tissue acidosis, a body cavity acidosis, or as a systemic acidosis. Further the method may be used to treat tissues such as esophageal tissue, corneal tissue or skin tissue that has been contacted by the alkali.

The $CO_2$ may be administered in a number of ways. For example, the $CO_2$ may be administered by causing the subject to inhale $CO_2$ gas. Where $CO_2$ gas is administered to the subject, it is administered in an amount sufficient to create an arterial $pCO_2$ greater than 40 millimeters of Mercury (mm Hg). Advantageously, the $CO_2$ gas is administered in an amount sufficient to create an arterial $pCO_2$ greater than 50 mm Hg, and more advantageously the $CO_2$ gas is administered in an amount sufficient to create an arterial $pCO_2$ between 55 and 63 mm Hg. Further, in the present invention, the $CO_2$ gas may contain up to 10% $CO_2$ by volume. Advantageously, the $CO_2$ gas consists essentially of 95% $O_2$ and 5% $CO_2$ by volume.

The method according to the invention is effective to combat damage to a tissue exposed to alkali material such as NaOH and KOH, including both liquid, such as aqueous liquid, and solid alkali material.

DETAILED DESCRIPTION OF THE INVENTION

Figure 1:
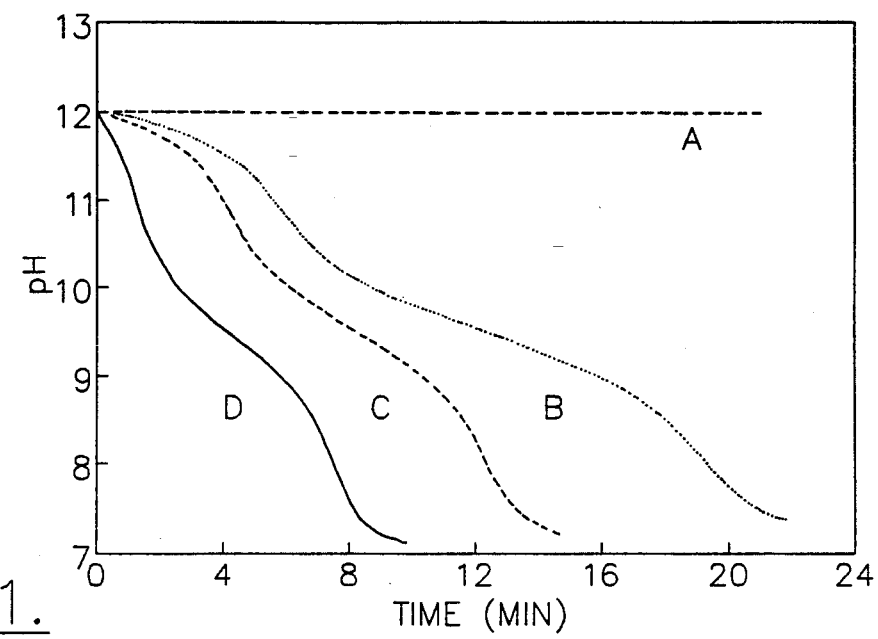
FIG. 1 demonstrates the ability of gas mixtures rich in $CO_2$ to rapidly reduce the alkalinity of a NaOH (lye)-containing solution in vitro.

The present invention provides a method for protecting stratified squamous epithelia-lined organs such as esophagus, skin and cornea, and other body tissues against damage from exposure to caustic alkaline substances such as NaOH and KOH. These substances damage tissues by means of their highly alkaline pH, thus the invention provides a method for protection by creating a mild acidosis within body tissues and body compartments. The mild acidosis protects body tissues from damage upon exposure to alkali by buffering (neutralizing) the alkali, thereby reducing pH rapidly to normal or near normal (innocuous) levels.

Generally, the invention involves the exogenous administration or local exposure to concentrations of $CO_2$ higher than that of room air to achieve a higher $pCO_2$ in tissues, blood, and body cavities. By raising tissue, blood, and body cavity $pCO_2$, a mild local and/or systemic (respiratory) acidosis is achieved via generation of carbonic acid See J. Piper. Pulmonary and circulatory carbon dioxide transport and acid-base homeostasis, in: *pH Homeostasis, mechanisms and control*, 181-202 (Haussinger Ed. 1988)(Academic Press Inc., San Diego, Calif.). Carbonic acid in turn serves to translate the $CO_2$ exposure into a beneficial therapeutic effect given the appropriate clinical circumstances.

In one model of the present invention, for example, inhalation of a 90% $O_2$/10% $CO_2$-room air/gas mixture results in arterial $pCO_2$ values higher than that achievable by breathing room air. Since arterial $CO_2$ readily diffuses, along its pressure gradient, into all body tissues and into the lumen of the intestinal tract, see Feldman GM, et al., *Amer. J. Physiol.* 9, G687-G694 (1984), the $pCO_2$ within esophageal tissues and lumen rapidly increases during such inhalation. Further $CO_2$ is a gas that produces, upon aqueous contact, a weakly acidic solution of carbonic acid ($H_2CO_3$); therefore increases in arterial $pCO_2$ to, for example, greater than 40 or even 50 millimeters of Mercury (mm Hg) will increase the rate and quantity of carbonic acid within esophageal tissues and esophageal lumen. In these locations carbonic acid can then act as a buffer (through rapid neutralization) of the noxious alkaline material, and in this way protect tissue from more extensive alkaline injury.

This method is also applicable to protection of the esophagus and other tissues against damage from alkali (NaOH or KOH) leaking from ingested commercial batteries. See T. L. Litovitz, *JAMA* 249, 2502-2504 (1983) and K. M. Kost and R. S. Shapiro, *J. Otolaryngol.* 16, 252-257 (1987). Moreover, this same method is applicable for the protection of the cornea and skin, among other tissues, against more severe injury as a result of alkaline exposure. For corneal or skin exposures, $CO_2$ therapy may be applied either locally by increasing the $pCO_2$ of the external atmosphere over the region involved or by delivering $CO_2$ to the region via the blood stream.

Such a mild acidosis can be rapidly and safely created within all body tissues and compartments by exposure to gas mixtures rich in $CO_2$ Specifically, the exposure to gas mixtures high in $CO_2$ can be achieved by inhalation of an atmosphere whose $CO_2$ concentration above that of room air. Higher concentrations of $CO_2$ than present in room air to affected parts of the body can be done in a variety of ways. These include rebreathing into a paper bag, inhaling fumes from dry ice, or breathing an atmosphere of 95% $O_2$/5% $CO_2$ (carbogen) or 90% $O_2$/10% $CO_2$, for example, by inhaling a $CO_2$-rich atmosphere delivered by nebulizer directly into the airway or inhaling a $CO_2$-rich atmosphere delivered into a face mask from a gas tank. Some alternative methods of increasing the $pCO_2$ within the body and its tissues include the ingestion or administration by rectal suppositories of capsules or cartridges containing $CO_2$-rich gas mixtures, among others. See, e.g., U.S. Pat. No. 3,121,663, hereby incorporated by reference, which teaches the use of carbon dioxide releasing laxative suppositories.

In a preferred embodiment, an individual that has ingested a caustic alkali or had caustic alkali splashed on their skin or into their eye would, after immediately washing externally accessible areas, seek access to a means to inhale a higher concentration of $CO_2$ than present in room air. This may initially entail the simple act of rebreathing into a paper bag, but, while emergency help is on its way and in the presence of a responsible adult, preferably would involve inhalation of a $CO_2$-rich gas (e.g. 95%$O_2$/5%$CCO_2$) delivered by gas tank and face mask or by nebulizer. As described for the therapy of retinal artery occlusion such inhalation should continue for ten minutes and then cease until help arrives but may be repeated every ten minutes each hour unless side effects are evident.

The invention has several advantages. It is relatively safe. Human volunteers have been shown to tolerate increases in arterial $pCO_2$ of 55-63 mm Hg during the breathing of $CO_2$-rich gas mixtures for at least 15-30 minutes without serious side effects (note: this reflects the fact that the acidosis created in tissues, body cavities and blood is mild in degree). See J. E. Remmers et al., *Respir. Physiol.* 4, 78-90 (1968) Inhalation of a $CO_2$-rich gas mixture known as carbogen (95%$O_2$/5%$CO_2$), for 10 minutes each hour at a 3 liter/hour flow rate, has been utilized for several years in the treatment of acute central retinal artery occlusion, see T. A. Deutsch et al., *Arch. Ophthalmol.* 101, 101:1278-1280 (1983) and D. L. Savitt, Therapeutic gases, in: *Emergency Drug Therapy*, 582-607 (W. G. Barsan, M. S. Jastremski, S. A. Syverud, Eds. 1991)(WB Saunders Company, Harcourt Brace Jovanovich, Inc., Philadelphia, Pa.). This recommendation is based on $CO_2$'s known ability to act as an arterial vasodilator, a mechanism fundamentally different from that forming the basis of $CO_2$ therapy for acute alkali exposures described in this report. Further the recognized ability of carbogen to produce an acidosis during treatment of retinal artery disease was considered an unwanted side effect. Moreover, in the event that side effects do develop from breathing carbogen or other $CO_2$-rich gas mixture, e.g. acidic taste, headache, dizziness, dyspnea, diaphoresis, paresthesias and apprehension, cessation of inhalation therapy rapidly leads to their dissipation. See D. L. Savitt, Therapeutic gases, supra.

Additionally its onset of action is rapid, and can be within seconds of inhaling the gas. It is effective. Thus even the mild acidosis produced in tissues, blood and body cavities results in rapid reduction in alkalinity and protection against deep tissue injury. The method is widely available in that gas distributors can equip tanks of virtually any size to deliver the gas in a wide range of settings. The method is also inexpensive. The only significant cost would likely be purchase of a reusable gas tank; alternatively a small inexpensive disposable product could be developed for one time usage.

Pharmaceutical formulations containing $CO_2$ are prepared by mixing the $CO_2$ with any pharmaceutically acceptable carrier, such as a gas tank. The term "pharmaceutically acceptable" means not deleterious to the subject being treated. While the present invention contemplates primarily the treatment of human subjects, it will be apparent that other animal subjects, particularly mammalian subjects such as horse, cat, dog, and cattle, may also be treated by the methods disclosed herein.

The present invention is explained in greater detail in the examples which follow. In the examples, "mg" means milligrams, "ml" means milliliters, "mm Hg" means millimeters of Mercury as a measurement of pressure, "$pCO_2$" means pressure of $CO_2$, and "kcal" means kilocalories. These examples are intended to be illustrative of the present invention, and are not to be construed as restrictive thereof.

EXAMPLE 1

Preparation of the in vivo Experimental Model

White New Zealand rabbits weighing between 8-9 lbs were anesthetized with a 1:1 mixture of diazepam (5 mg/ml) and pentobarbital sodium (60 mg/ml) and a tracheostomy tube was inserted. The esophagus was cannulated in the neck and above the esophagogastric junction. The esophageal cannula in 0the neck was connected via polyvinyl tubing to a Buchler polystatic pump so that solutions (isotonic saline or isotonic saline pH'd to alkaline levels with NaOH) could be perfused through the esophagus. The distal esophageal cannula emptied directly into a beaker to collect the esophageal drainage. In some experiments the esophageal perfusate entering and, again, upon leaving the esophagus was drawn into a syringe and placed on ice for measurements of $pCO_2$. In other experiments, a Y-cannula was inserted into the esophagus at the neck in order to permit perfusion through one limb and insertion of either a pH microelectrode or potential difference probe through the other and into midesophagus. The pH microelectrode was used to monitor intraluminal pH continuously during and after perfusion with alkaline solutions, and the potential difference probe was used to determine the functional integrity of the tissue before and after exposure to noxious concentrations of alkali.

For studying the effects of inhaling an atmosphere rich in $CO_2$, some animals had an open shield placed over the tracheostomy port across which flowed a gas mixture of 90%$O_2$/10%$CO_2$. This gassing mixture was used because the increase in arterial $pCO_2$, approximately 15-20 mm Hg as determined by blood gas analysis, was comparable to that of humans breathing carbogen (95%$O_2$/5%$CO_2$). Further, since preliminary experiments demonstrated that short term (less than 1 hour) exposures of the esophageal epithelium to alkaline pH values $\leq 10.5$ were not damaging, experiments such as those showing the neutralization effects of breathing room air versus $CO_2$-rich gas mixtures in the same animal were performed using alkaline solutions whose pH values were below this level.

EXAMPLE 2

Gas Mixtures Rich in $CO_2$ Rapidly Reduce the Alkalinity of a NaOH-Containing Solution In Vitro A $CO_2$-rich gas mixture was bubbled into a solution made alkaline by addition of NaOH. FIG. 1 demonstrates the ability of gas mixtures rich in $CO_2$ to rapidly reduce the alkalinity of a NaOH (lye)-containing solution. The experiment, which is performed in vitro, shows that compared to exposure to air, bubbling $CO_2$-rich gas mixtures (95%$O_2$/5%$CO_2$ or 90%$O_2$/10%$CO_2$) into 10 cc of an unbuffered saline solution made alkaline by the addition of NaOH results in rapid reduction (within minutes) of pH to innocuous levels and that increasing the concentration or flow rate of the bubbled $CO_2$-rich gas mixture entering the solution substantially increases the rate of reduction in alkalinity. [Note: 10 cc was used as a convenient volume to study but has little relevance to the clinical situation in which the actual residual volume of alkali to be buffered within esophagus may be closer to 1-3 ml, the majority of the bolus being cleared within seconds after exposure by gravity and swallow-initiated peristalsis (4)]. Data presented is representative of 3 experiments.

EXAMPLE 3

Figure 2:
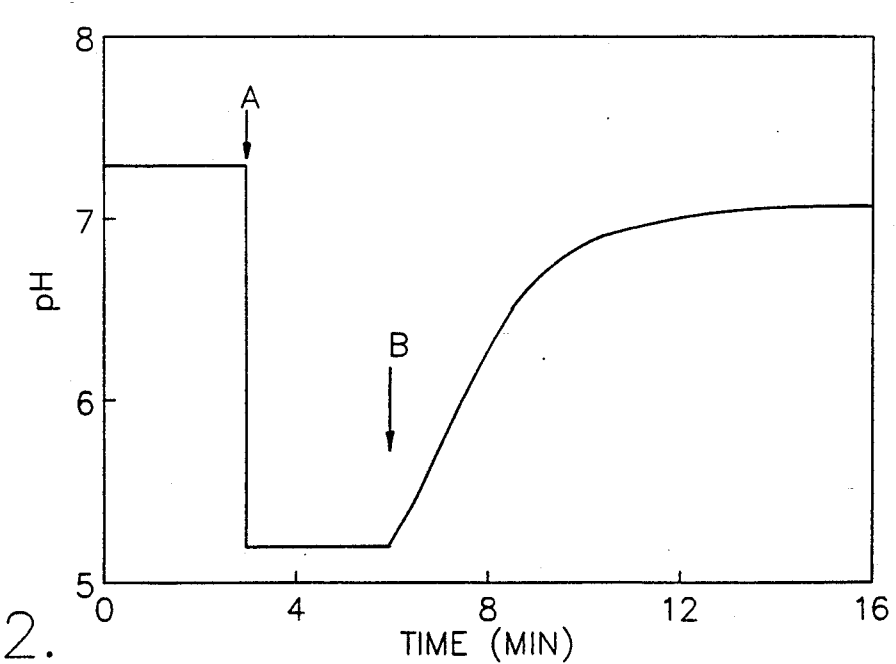
FIG. 2 demonstrates in vivo that endogenous $CO_2$ in animals, partial pressure in arterial blood ($pCO_2$) of 33-45 mm Hg, readily traverses the wall of the esophagus to acidify the esophageal luminal contents.

Endogenous $CO_2$ Carried by Blood at a Partial Pressure of 38-40 mm Hg Can Diffuse Across the Wall of the Esophagus to Acidify the Esophageal Luminal Contents FIG. 2 demonstrates that endogenous $CO_2$ in animals, partial pressure in arterial blood ($pCO_2$) of 33-45 mm Hg, readily traverses the wall of the esophagus to acidify the esophageal luminal contents. In this experiment, a diazepam-pentobarbital-anesthetized rabbit has its esophagus perfused with an unbuffered isotonic saline solution whose initial pH outside the animal was 7.4. Immediately upon initiation of perfusion, the solution leaving the esophagus is observed to have become significantly more acidic, pH of approximately 5.3. In FIG. 2 the unbuffered esophageal perfusate (A), isoosmotic saline with perfusion rate =5 ml/min, is shown to be rapidly acidified as it exits the esophagus (B), an acidification that is reversed by gassing the perfusate with $CO_2$-free nitrogen.

The cause for this rapid acidification is demonstrated to be the result of entry of a volatile acidifying substance, and specifically $CO_2$, since the $pCO_2$ of the perfusate increases and the solution's pH can be returned back to initial pH by gassing the solution with $CO_2$-free nitrogen (nitrogen drives off the $CO_2$ dissolved in solution). Data presented is representative of 5 experiments.

EXAMPLE 4

Figure 3:
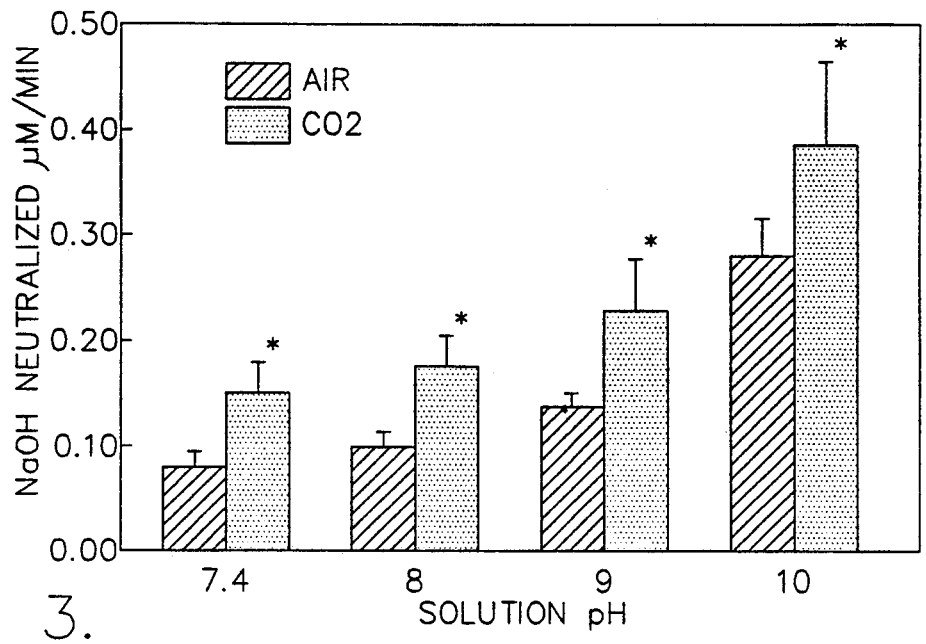
FIG. 3 demonstrates in vivo that the $CO_2$-induced acidification of a solution passing through the rabbit esophagus can rapidly and effectively neutralize the alkalinity of esophageal luminal contents, and further that the rate of neutralization of the alkalinity can be enhanced by having the animal breathing a gas mixture rich in $CO_2$ (90% $O_2$/10% $CO_2$) as compared to breathing room air (0.03% $CO_2$). The greater the degree of luminal alkalinity, the more rapid the rate of neutralization by carbon dioxide.

Luminal Acidification Induced by the Diffusion of the Neutralizes Alkali in Vivo FIG. 3 demonstrates in vivo that the $CO_2$-induced acidification of a solution passing through the rabbit esophagus can effectively neutralize the alkalinity of esophageal luminal contents, and further that the rate of neutralization of an alkaline solution being recirculated through the rabbit esophagus by carbon dioxide entering the lumen is increased in rabbits inhaling a carbon dioxide-rich gas mixture (90%$O_2$/5%$CO_2$) as compared to breathing room air (0.03%$CO_2$). The greater the degree of luminal alkalinity, the more rapid the rate of neutralization by carbon dioxide. The data of FIG. 3 illustrates the rate of luminal titration of 30 cc of an isoosmotic alkaline solution (pH between 7.4 and 10.0) as it is recirculated through the rabbit esophagus in vivo. These results were significant at the $p < 0.05$ level.

Figure 4:
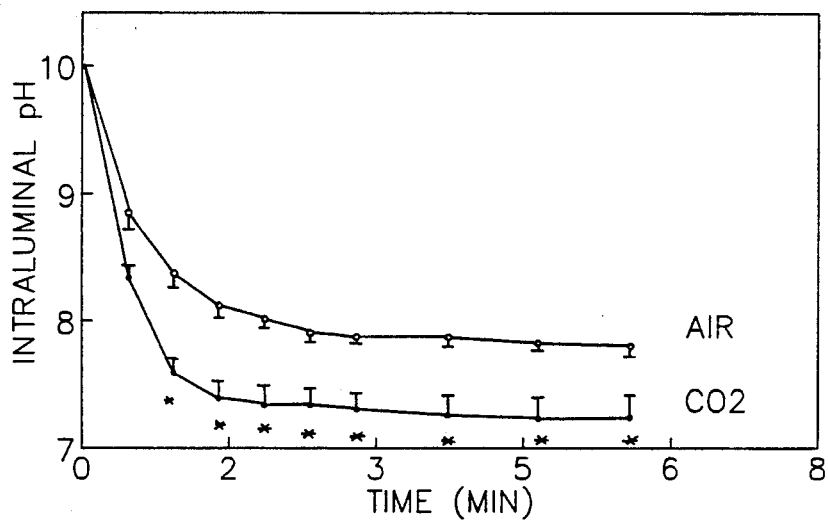
FIG. 4 demonstrates that breathing a $CO_2$-rich atmosphere more rapidly reduces an alkaline luminal pH (pH 10) toward neutrality than breathing room air and this rate is on the order of minutes.

FIG. 4 also demonstrates the same principle but shows in addition that when the clinical situation is mirrored by allowing the alkaline volume to be spontaneously cleared from the esophagus, the rate of neutralization of alkaline contents is very rapid. This is illustrated in vivo by perfusing the rabbit esophagus with an isotonic saline solution titrated to alkaline pH of 10.0 with NaOH. After reaching a steady pH of 10 within the esophageal lumen, the solution was allowed to drain spontaneously while rate of recovery in intraluminal pH was monitored by intraluminal pH microelectrode.

As shown FIG. 4, endogenous clearance of the luminal alkali by drainage and titration of alkali by diffusion of endogenous $CO_2$ was rapid with the animal breathing room air but that when the same animal was breathing a $CO_2$-rich gas mixture (90%$O_2$/10%$CO_2$-room air combination), the rate of neutralization of the alkaline solution was at least 50% faster. Note: the faster rate of reduction in solution alkalinity was shown to be due to entry of $CO_2$ by documenting in some experiments that upon breathing the $CO_2$-rich gas mixture, an increase in arterial $pCO_2$ (average increase to 58 mm Hg) occurs along with an increase in perfusate $pCO_2$. Also a pH 10 alkaline solution was chosen so that the same animal could be used for comparing the rate of reduction in pH breathing room air and a carbon-dioxide rich gas mixture because this pH was found not to damage the esophagus over the time periods in this study. Further, similar differences in rates of reduction in pH of the alkaline solution within the esophagus occur while breathing room air or the $CO_2$-rich gas mixture regardless of the order of inhalations. Data represent the mean ±SEM for 4 paired inhalations in 1 rabbit and is representative of experiments performed in 4 different rabbits. These results were significant at the $p < 0.05$ level.

The model documents that acute administration of exogenous $CO_2$, in this model in the form of inhalation of an atmosphere containing 90%$O_2$/10%$CO_2$-room air gas mixture, to animals whose esophagi have been exposed to NaOH, rapidly reduces the potentially noxious alkaline pH of esophageal luminal contents toward neutrality.

EXAMPLE 5

Figure 5:
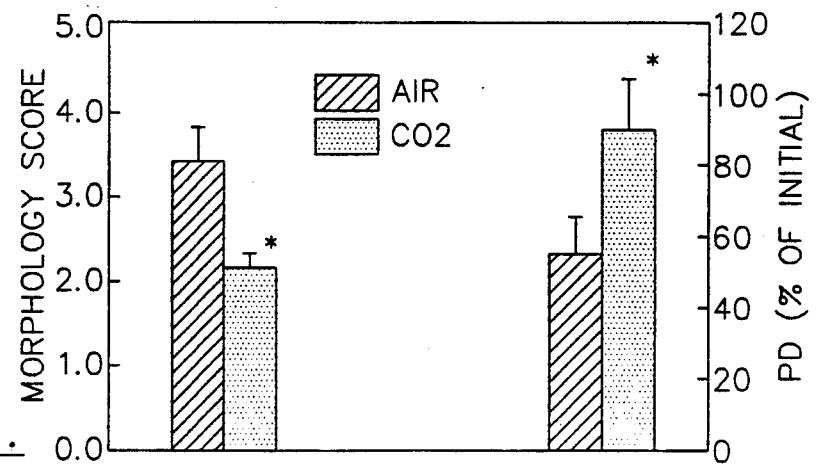
FIG. 5 demonstrates in vivo that breathing a $CO_2$ rich gas mixture provides both morphologic and functional (potential difference) protection to alkali exposed tissues.

Increased Delivery of $CO_2$ Reduces Alkali Damage the Esophageal Epithelial Lining FIG. 5 documents by microscope examination and functional (potential difference) characteristics of the tissue that the esophageal epithelial-lining of an animal breathing a carbon-dioxide rich gas mixture is more effectively protected against injury upon exposure to alkali than one breathing room air. The normal esophageal epithelial lining of the rabbit was examined for comparison. Note: from morphology of tissues (data not shown) that in the animal breathing the $CO_2$-rich gas mixture the basal layers (stratum germinativum) which are the only ones capable of replication in esophageal epithelium are preserved while in one third of the animals breathing room air there is transepithelial necrosis—an event capable of initiating fibrosis and stricture formation.

In this experiment the diazepampentobarbital-anesthetized rabbit had its esophagus perfused for 15 minutes with an isotonic saline solution whose pH was 11.75 (titrated to 11.75 with NaOH). The solution was not recirculated and so esophageal exposure to pH 11.75 was maintained for the entire period of time. Half of the experimental animals were exposed to the alkaline solution while breathing room air and the other half of the animals were exposed to the alkaline solution while breathing a $CO_2$-rich gas mixture (90%$O_2$/10%$CO_2$-room air mix). The $CO_2$-rich gas mixture was created by gassing the atmosphere over a tracheostomy tube partially enclosed by a face mask-like shield. The shield, however, was not completely enclosed and so did not prevent room air from mixing with the 90%$O_2$/10%$CO_2$ gas flowing by it. This gassing mixture was used because the increase in arterial $pCO_2$, approximately 15-20 mm Hg as determined by blood gas analysis, was comparable to that of humans breathing carbogen (95%$O_2$/5%$CO_2$).

Before perfusion of alkali esophageal potential difference was measured and thus repeated after perfusion was stopped. After perfusion, the animals were euthenized with an overdose of pentobarbital, and the esophagus was excised and inspected grossly for lesions. A mid-section of the esophagus was then removed, placed in fixative (2% paraformaldehyde, 4% glutaraldehyde in 0.1N phosphate buffer, pH 7.4) and stained with hematoxylin and eosin for histologic evaluation. Morphologic injury was assessed by an observer unaware of the treatment category. The following scoring system was employed: 0=normal, 1+ =scattered superficial (upper 1/3rd of epithelium) necrosis, 2+ =uniform superficial necrosis, 3+ =scattered deep (but not transepithelial) necrosis, 4+ =uniform deep (but not transepithelial) necrosis, 5 =transepithelial necrosis. The results as illustrated above indicated that 3/8 animals breathing room air had transepithelial injuries while none of the eight breathing the $CO_2$-rich gas mixture had such deep injuries. Mild surface injury was seen in all but one animal breathing $CO_2$-rich gas mixtures while similar mild injury was seen in only 3 of the 8 animals breathing room air. The remaining 2 animals breathing room air and 1 animal breathing $CO_2$-rich gas mixtures had injuries more severe than surface injuries but not completely transepithelial.

Using the Wilcoxon signed ranks test for non-parametric data and student's t test for parametric data, these results were significant at the $p<0.05$ level. Therefore neutralization of alkali by these higher concentrations of $CO_2$ was apparently capable of reducing the noxious levels of luminal alkali from penetrating and producing severe tissue injury.

The model documents that acute administration of exogenous $CO_2$, in this model in the form of inhalation of an atmosphere containing 90%$O_2$/10%$CO_2$-room air gas mixture, to animals whose esophagi have been exposed to NaOH, both rapidly reduces the potentially noxious alkaline pH of esophageal luminal contents toward neutrality and significantly reduces the severity (depth) of esophageal tissue necrosis.

By reducing the depth of esophageal epithelial injury and with preservation of the replicating basal cell layer and basement membrane, it is anticipated that $CO_2$ therapy would also reduce the major risk of esophageal damage which is stricture formation. Through the same mechanisms by which $CO_2$ therapy protects against alkali injury to esophagus, it should also be capable of minimizing injury to other tissues of the body, e.g. cornea and skin, after toxic exposures to alkali.

EXAMPLE 6

Neutralization of Alkali by $CO_2$-rich Gas Results in Only Small Increases in Temperature Neutralization of alkali by these higher concentrations of $CO_2$ did not increase tissue injury (a theoretical concern based on the neutralization of alkali by acids producing a damaging exothermic reaction) as well as was apparently capable of reducing the noxious levels of luminal alkali from penetrating and producing severe tissue injury. A concern previously raised about ingesting an acid to neutralize the ingested alkali is that the neutralization reaction would produce heat (exothermic reaction) and the heat may be great enough to damage tissues.

Figure 6:
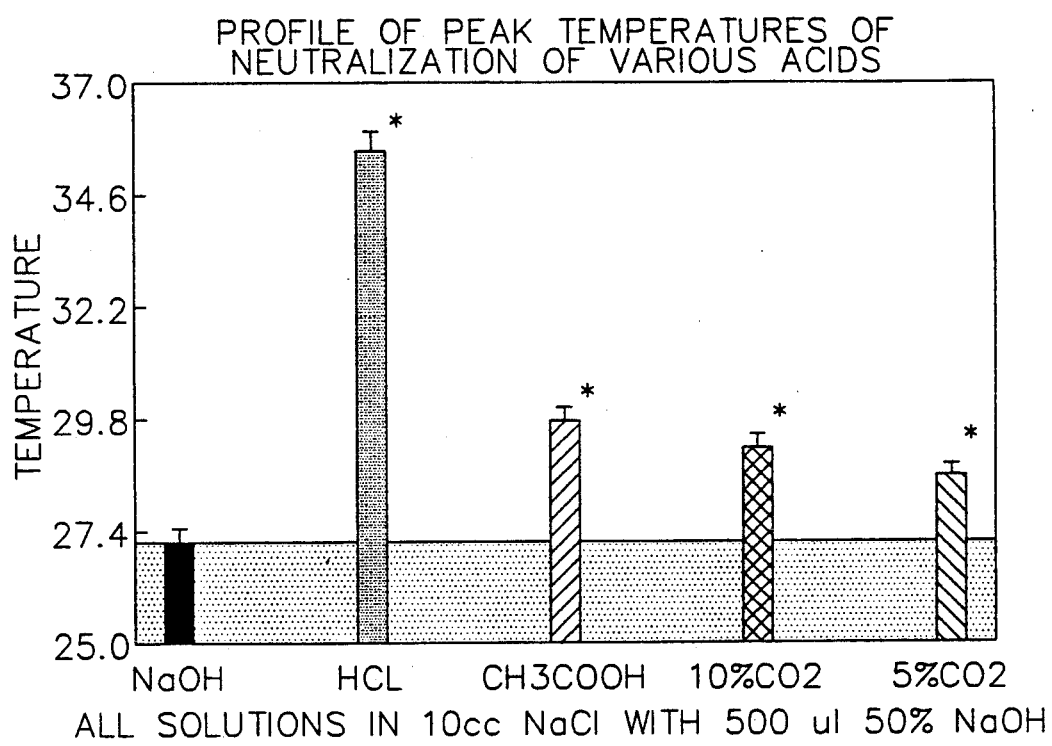
FIG. 6 demonstrates the maximum temperature increase of an alkaline solution of NaOH during its neutralization by addition of either strong or weak acids.

Neutralization of a strong alkali like NaOH with a strong acid like HCl since this reaction gives off 13.3 kcal/mole and can raise temperature approximately 9 degrees as shown in FIG. 6. FIG. 6 shows the maximum temperature increase of an alkaline solution of NaOH during its neutralization by addition of either strong or weak acids. When NaOH is solubilized in an aqueous solution a heat of reaction occurs that increase the background temperature of the solution (shade area).

However, when NaOH is neutralized by acid, depending on the ionization strengths of the acid, different amounts of heat are liberated resulting in greater increases in solution temperature than that of solubilization alone. The heat of neutralizing NaOH by carbonic acid formed by the solubilization of $CO_2$ results in the lowest rise in temperature, approximately 1-2 degrees depending on concentration inhaled. For acetic acid, the maximum temperature increase was approximately 3 degrees. Thus when NaOH is neutralized by a weak acid such as acetic acid or carbonic acid, the heat liberated is much less because a heat of ionization is required to remove the hydrogen from weak acids. This reaction is endothermic, thus less heat is available to raise the solution or tissue temperature. Such small increases in temperature produce no significant risk of tissue damage. [Note: although Rumack et al. caution against the use of weak acids to neutralize alkali because of the potential for excess heat production to increase tissue injury, they showed that only lemon juice, as the weak acid, but not acetic acid, produced more heat on contact with alkali than did water. Thus, their data are often mistakenly quoted to indicate that all attempts at neutralization of alkali by acid are dangerous and without benefit. The data herein described clearly demonstrate that this is not the case. (Rumack BH, Burrington JD. Caustic ingestions: a rational look at diluents. Clin Toxicol 1977;11(1):27–34).] In addition, since $CO_2$ is a readily diffusible gas with access to virtually all tissues and cavities of the body, its effectiveness upon inhalation in reducing damage from alkalinity within the esophagus would be fully expected to protect against alkaline damage to other parts of the body, notably skin and eye.

EXAMPLE 7

Carbon Dioxide Administered to a Human Subject Via a $CO_2$-rich Gas Diffuses Across the Wall of the Esophagus Carbon dioxide administered by a $CO_2$-rich gas to a human subject also enters the lumen of the human esophagus. In four experiments conducted with human volunteers, an esophageal segment was isolated by a double-balloon technique. The segment was perfused through a catheter port with a solution of saline containing a $pCO_2$ of less than 0–1 mm Hg. The perfusate was aspirated from the esophagus within 1–2 minutes and found upon repeat measurements to contain a $pCO_2$ of 10±1 mm Hg. This increase in $pCO2$ of the solution documents that like the rabbit esophagus, the lumen of the human esophagus takes up carbon dioxide, and as such carbon dioxide is available for tissue and luminal buffering of any ingested alkali.

While the foregoing invention has been described in some detail for purposes of clarity and understanding, it will be clear to one skilled in the art from a reading of this disclosure that various changes in form and detail can be made without departing from the true scope of the invention.

There are three additional advantages of inhalation of $CO_2$ over the ingestion of a weak acid for the treatment of lye ingestion. First, as opposed to ingesting weak acids where there is no guarantee that the acid would be delivered to the area of alkaline burn, the gradient driven entry of $CO_2$ into tissue ensures that it is present in great amounts in areas of greatest alkalinity; second, because it is gradient driven, $CO_2$ inhalation is unable to overshoot and thereby incapable of producing unwanted and excessive acidity in a previously alkaline-damaged, but subsequently neutralized, region; and third $CO_2$ neutralizes from inside out, that is, it protects against the alkaline front advancing into the tissue while luminal acid must attempt to catch the front from behind (luminal side) in order to afford protection to deeper layers.

That which is claimed is:

1. A method for combatting caustic damage to gastro-intestinal tissue caused by contact of that tissue to an alkali material in a subject in need of said treatment, the method comprising administering to the airways of said subject about 5% to about 10% gaseous $CO_2$ in a pharmaceutically acceptable carrier in a therapeutically effective amount to produce an acidotic state, the acidotic state serving to prevent caustic alkali damage to the tissue.

2. A method according to claim 1, wherein said acidotic state is a tissue acidosis.

3. A method according to claim 1, wherein said acidotic state is a body cavity acidosis.

4. A method according to claim 1, wherein said acidotic state is a systemic acidosis.

5. A method according to claim 1, wherein said subject is a mammal.

6. A method according to claim 1, wherein said subject is a human subject.

7. A method according to claim 1, wherein said $CO_2$ is administered by causing said subject to inhale $CO_2$.

8. A method according to claim 1, wherein said tissue is the esophagus.

9. A method for combatting caustic damage to esophageal tissue caused by the ingestion of a caustic alkaline material by a subject, the method comprising causing said subject to breath a gas containing about 5% to about 10% gaseous $CO_2$ in a pharmaceutically acceptable carrier in a therapeutically effective amount to produce an acidotic state, the acidotic state serving to prevent caustic alkali damage to the esophageal tissue.

10. A method according to claim 9, wherein said alkali material is selected from the group consisting of NaOH and KOH.

11. A method according to claim 9, wherein said alkali material is selected from the group consisting of liquids and solids.

12. A method according to claim 9, wherein said alkali material is an aqueous liquid.

13. A method according to claim 9, wherein said gas is administered in an amount effective to create an arterial $pCO_2$ greater than 50 mm Hg but no greater than about 63 mm Hg.

14. A method according to claim 9, wherein said gas is administered in an amount effective to create an arterial $pCO_2$ from 55 to 63 mm Hg.

15. A method according to claim 9, wherein said gas consists essentially o 95% $O_2$ and 5% $CO_2$ by volume.

16. A method for combatting caustic damage to esophageal tissue caused by the ingestion of a caustic alkaline material by a subject, the method comprising causing said subject to breath a pharmaceutically acceptable gas carrier containing about 5% to about 10% gaseous $CO_2$ by volume in a therapeutically effective amount to create an arterial $pCO_2$ pressure sufficient to produce an acidotic state but no greater than about 63 mm Hg, the acidotic state serving to prevent caustic alkali damage to the esophageal tissue.

17. A method according to claim 16, wherein said gas is administered in an amount effective to create an arterial $pCO_2$ greater than 50 mm Hg but no greater than about 63 mm Hg.

* * * * *

UNITED STATES PATENT AND TRADEMARK OFFICE
CERTIFICATE OF CORRECTION

PATENT NO. : 5,262,180

DATED : 16 November 1993

INVENTOR(S) : Roy C. Orlando and R. Lee Meyers

It is certified that error appears in the above-identified patent and that said Letters Patent is hereby corrected as shown below:

Column 1, Line 6, correct "DK 35013" to read --DK 36013--.

Column 7, line 33, after "Diffusion of" add --$CO_2$--

Signed and Sealed this

Fourteenth Day of June, 1994

Attest:

BRUCE LEHMAN

*Attesting Officer*   *Commissioner of Patents and Trademarks*